United States Patent [19]

Seth et al.

[11] Patent Number: 4,721,709
[45] Date of Patent: Jan. 26, 1988

[54] NOVEL PHARMACEUTICAL COMPOSITIONS CONTAINING HYDROPHOBIC PRACTICALLY WATER-INSOLUBLE DRUGS ADSORBED ON PHARMACEUTICAL EXCIPIENTS AS CARRIER; PROCESS FOR THEIR PREPARATION AND THE USE OF SAID COMPOSITIONS

[76] Inventors: Pyare Seth, Krebsenbachweg 8, Aesch 4147, Switzerland; Pawan Seth, 11 Guru Sarday Road, Calcutta 700019, India

[21] Appl. No.: 893,106

[22] Filed: Aug. 4, 1984

Related U.S. Application Data

[63] Continuation-in-part of Ser. No. 759,052, Aug. 27, 1985, abandoned.

[30] Foreign Application Priority Data

Jul. 26, 1984 [CH] Switzerland ............... 3623/84

[51] Int. Cl.$^4$ ............................................ A61K 31/55
[52] U.S. Cl. .................................................. 514/221
[58] Field of Search ........................................ 514/221

[56] References Cited

FOREIGN PATENT DOCUMENTS 0124027 7/1984 European Pat. Off. .

OTHER PUBLICATIONS

Merck Index, 9th Ed. (1976), p. 898.
Chem. Abst. 99-27931K (1983); 99-110596A (1983) and 100-1978175 (1984).
Tulakhar et al; J. Pharm. Pharmacol, 1983, 35:269-274.
Sandersen et al., J. Pharm. Pharmacol, 1984, 36 789-795.

Primary Examiner—Stanley J. Friedman
Attorney, Agent, or Firm—Bert J. Lewen; Henry Sternberg

[57] ABSTRACT

Pharmaceutical compositions are disclosed which contain hydrophobic practically water-insoluble drugs adsorbed onto carriers such as starch and/or microcrystalline cellulose. The rate of dissolution and absorption in the body is improved due to the very fine particle size of the drug adsorbed onto the carriers. The drug particles have a mean size of less than 10 microns the size distribution of particles being such that at least 95% of particles are smaller than 15 microns. A process for the preparation of drug-carrier adsorbates and their incorporation in pharmaceutical compositions is also disclosed. The use of such compositions to treat mammals is also disclosed.

28 Claims, 3 Drawing Figures

FIG. I
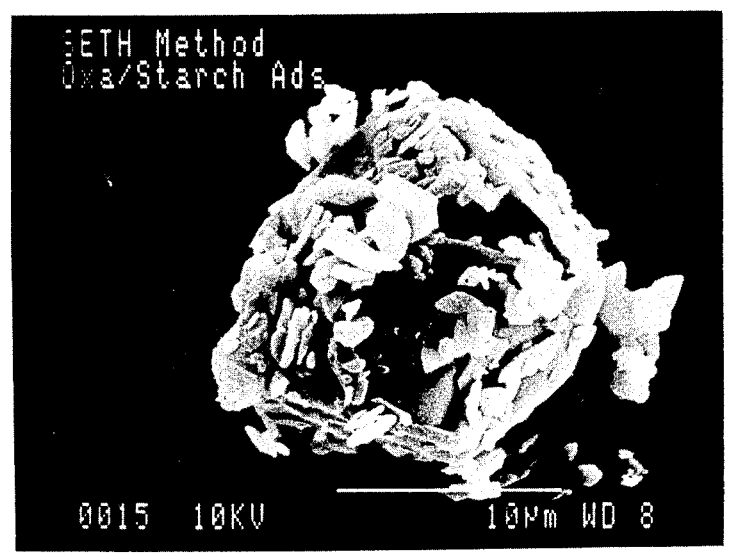
FIG. 2
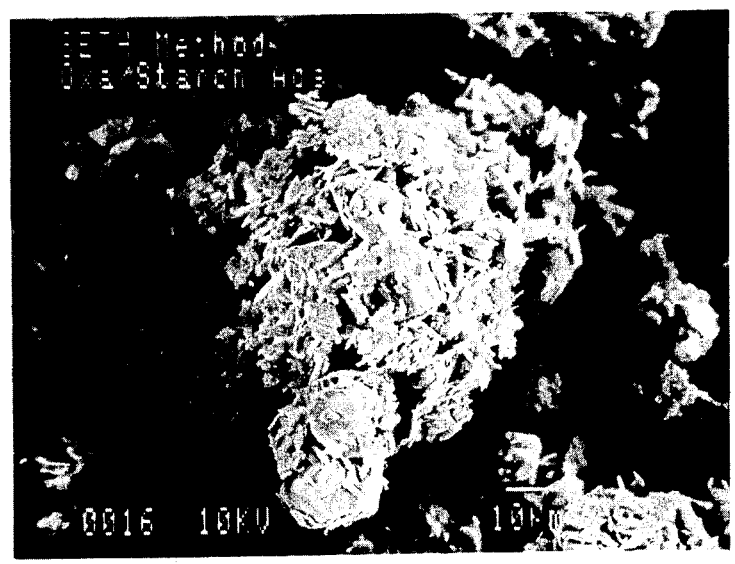

NOVEL PHARMACEUTICAL COMPOSITIONS CONTAINING HYDROPHOBIC PRACTICALLY WATER-INSOLUBLE DRUGS ADSORBED ON PHARMACEUTICAL EXCIPIENTS AS CARRIER; PROCESS FOR THEIR PREPARATION AND THE USE OF SAID COMPOSITIONS

CROSS REFERENCE TO RELATED APPLICATIONS

This application is a continuation-in-part of our co-pending application Ser. No. 759,052 filed Aug. 27, 1985, now abandoned entitled "Novel Oxazepam containing pharmaceutical composition, process for the preparation of an active ingredient therefore and the use of said composition".

DISCUSSION OF REFERENCES IN FILE OF EARLIER COPENDING APPLICATIONS

In the Merck Index 9th Edition 1976, p. 898 the substance oxazepam is disclosed and its use us given as a tranquilizer.

In Chem. Abs., 99-27931K (1983); 99-110596A (1983) and 100-1978175 (1984) microencapsulated benzodiazapines and rapidly disintigrating benzodiazepine tablets are disclosed. These earlier methods do not give a greatly accelerated onset of action of the benzodazepine active ingredient.

TECHNICAL FIELD OF THE INVENTION

The present invention relates to pharmaceutical compositions having improved rate of dissolution containing as an active ingredient a drug that is very slightly soluble or practically insoluble in water, by adsorption on pharmaceutical excipients such as starch and/or microcrystalline cellulose to act as carriers. The present invention also relates to a process for the preparation of drug adsorbates which are incorporated in pharmaceutical compositions for preparing various dosage forms and also the use thereof.

DEFINITION

There are large numbers of drug substances that are very slightly or practically insoluble in water. According to the U.S. Pharmacopeia (U.S.P.) XXI (page 1441) a drug substance is described as 'very slightly soluble' if one part of solute (drug substance) requires from 1,000–10,000 parts of solvent to dissolve it and as 'practically insoluble' if one part of solute requires more than 10,000 parts of solvent to dissolve it or its solubility is less than 0.1 mg/ml of solvent. In the reference tables on the approximate solubility of various drug substances given on pages 1483–1490 of U.S.P. XXI there is given a list of quite a number of drugs that are 'very slightly soluble' or 'practically insoluble' in water. In the following is a representative list of some typical such drugs: allopurinol, acetohexamide, benzthiazide, chlorpromazine, chlordiazepoxide, haloperidol, indomethacine, lorazepam, methoxsalen, methylprednisone, nifedipine, oxazepam, oxyphenbutazone, prednisone, prednisolone, pyrimethamine, phenindione, sulfisoxazole, sulfadiazine, temazepam, sulfamerazine, trioxsalen.

BACKGROUND OF THE INVENTION

It is a common observation that when poorly soluble, hydrophobic drug substances are employed in the preparation of solid dosage forms such as tablets or capsules, their rate of dissolution is rather slow. As a result, their absorption from the gastrointestinal tract into systemic blood of the body is also slow. However, if such drugs are to be administered in oral dosage forms and to be used for clinical indications where a rapid onset of therapeutic activity is desirable, the slow rate of dissolution and slow rate of absorption can put very great limitations on their therapeutic utility.

A frequently used method to overcome such problems is to finely grind or 'micronise' drug substances so as to reduce their particle-size. For example high speed running pin mills or air-jet mills are used to reduce the particle-size to a range of 5–10 microns. A major disadvantage of such grinding methods is the resulting tendency of the milled particles to agglomerate and the formation of an electrostatic charge on their surfaces which leads to poor flow and wetting of the particles. These disadvantages may even negative the very purpose of obtaining a faster rate of dissolution by the particle-size reduction. (Aguiar et al. Journal Pharm. Sci. 1967, 56, page 1243- and Monkhouse et al. Journal Pharm. Sci. 1972, 61, page 1430 et. seq.).

One highly useful class of drugs is the benzodiazepines. These are mostly used as sedatives and tranquilisers. Almost all members of this class of drugs, with few exceptions, are practically insoluble or very slightly soluble in water. Their formulation into oral solid dosage-forms presents a general problem. It is also known that among the various benzodiazepines large differences exist with regard to their metabolism and pharmacokinetic properties. (Breimer et al. Drug Research 1980, 30 (1) no. 5a, page 875-). Some benzodiazepine drugs such as diazepam and flurazepam are eliminated from the body at a relatively slow rate with formation of active metabolites. Others such as temazepam and oxazepam are metabolised rather rapidly and without the formation of active metabolites. These differences are clinically important since pharmacokinetic factors determine the duration of action of a drug and also the dosage required. In making use of a drug in different clinical indications, the required duration of their action may be very different. In case of antianxiety or anticonvulsant therapy there is a need for continuous treatment which may extend over a long period of time. There is hence a need for parent drugs or those having active metabolites with a long elimination half-life. On the other hand if a drug is to be used as a hypnotic it is desirable that a drug with a shorter half-life and whose duration of action can be restricted to the night be used preferably. This can ensure that no hangover effects of sedation are felt on awakening the following day.

Ideally drugs and pharmaceutical compositions containing them, to be used as hypnotics should have the following properties:

(a) a rapid onset of activity following their administration (b) the activity should last for a period corresponding to that of normal sleep duration of 8–10 hours.

(c) there should be a minimum residual sedation after a period of 10 to 12 hours so that the subject can attend to his/her normal daily routine after awakening.

Although most of the benzodiazepine drugs are used as tranquilisers and sedatives, a few members of this class have been used as hypnotics. Nitrazepam and flurazepam are the typical examples of compounds that have been employed as hypnotics. However, due to their long half-life and the formation of active metabolites they are reported to cause the typical 'side effects' of sedation and morning hangover. Another benzodiazepine compound with an intermediate half-life that has recently been increasingly used as hypnotic is temazepam (7 chloro-1,3 dihydro-3-hydroxy-1, methyl-5 phenyl-2H-1,4 benzodiazepine-2-one). Due to its pharmacokinetic profile and little formation of active metabolites it has been found to be a very suitable hypnotic; however, due to its poor solubility the marketed hard gelatine dosage-form has been said to be not satisfactory. A publication (Fucella et al. Europ. Jour. Clin. Pharmacol. 1977, 12, pages 383-386) reported that a soft gelatine capsule formulation containing the drug in dissolved form showed a relatively faster absorption and a shorter time to reach peak blood concentration as compared to a hard-gelatine capsule formulation containing the drug in powder form. There has also been reported an inconsistent efficacy of this drug compound when contained in a hard gelatine capsule formulation (Miller, Pharmacotherapy, 1981, 1, pages 3–13).

Another similar benzodiazepine drug with an intermediate half-life (ca. 8–12 hours) is oxazepam (7-chloro-1,3 dihydro-3-hydroxy-5-phenyl-2H-1,4 benzodiazepine-2-one). It is available in the U.S.A. under the name Serax (Wyeth Laboratories) in dosage strengths of 10, 15 and 30 mg in the form of hard gelatine capsules and also as a 15 mg tablet. In several European countries however it is sold under the name Seresta as a 15 mg tablet and Seresta Fort as a 50 mg tablet. The therapeutic use of oxazepam as a tranquiliser is very well established but its use as a hypnotic has been a matter of controversy. In the year 1980 the British Committee on Review of Medicines published guidelines for the therapeutic use of various benzodiazepine drugs (British Medical Journal, Mar. 28, 1980, page 912). It was specifically mentioned therein that oxazepam is not to be recommended for hypnotic use but only as a tranquiliser. In some other countries like France, however, oxazepam in the form of Seresta Fort (50 mg) tablets is occasionally used as a hypnotic with the result that side effects of sedation and next morning sedation are frequently observed. Since oxazepam is practically insoluble in water and has a slow rate of dissolution and absorption, it also results in a longer time for the onset of sleep. It could perhaps be used as a good hypnotic provided it were possible to increase its rate of dissolution by either a formulation or some other method. This may eventually also enable the use of an optimal lower dose of oxazepam as a hypnotic than Seresta Fort as 50 mg tablets and thus reduce the incidence of side effects observed with the present dosage form.

It is hence an object of this invention to develop an improved solid dosage-form (capsule or tablet) containing oxazepam in a dose lower than 50 mg which shows rapid dissolution and absorption and thus a shorter time for sleep induction by rapidly achieving the equivalent maximum blood concentration to that reached more slowly by Seresta Fort, so that oxazepam can be used as a hypnotic. A further aim of this invention is to develop a process which is applicable in general to almost all or most of the "practically water insoluble drugs" so that they can be easily formulated into solid dosage-forms showing a fast rate of dissolution and absorption.

As has been mentioned above a conventional method for increasing the rate of dissolution of solids is by reduction of their particle size by micronisation or similar dry grinding methods. This, however, often leads to agglomerate formation of the milled product due to its poor wetting properties and is not helpful in increasing dissolution. Other approaches adopted to overcome these problems involve formation of "solid dispersions or solid-solid solutions". This involves the melting together of the drug and excipients such as sugars, urea, or polyvinylpyrrolidone etc. (J. L. Ford, Pharm. Acta Helvetica, 1986, 61, (3), 69–88 "The current status of solid dispersions"). Another approach has been to form "inclusion compounds" of some drugs by their complexation with cyclodextrines (Uekama K. et al. Internat. Jour. Pharmaceutics, 1983, 16, pages 327–388). Both the above mentioned processes are applicable to a few drugs and also only to a very limited extent. The comprehensive literature review by J. L. Ford refers to more than 120 drugs that have been used in the evaluation of solid-dispersion techniques.

Another technique that has been extensively used in the field of analytical chemistry of "adsorption chromatography" makes use of adsorption of drugs on some inorganic carriers such as silicates and some special types of aluminates etc. Some workers have also applied this method to investigate the adsorption of certain drugs on such inorganic supports having a large "internal porous surface area" so that their dissolution rate and solubility could be increased by desorption in the dissolving medium. The adsorption properties of drugs on such carriers however, depend mainly on the functional groups present as also the internal surface area and the pore volume of the support materials employed (Rupprecht H., Progr. Coll. and Polymer Sci., 1976, 60, 194–202). A few studies employing Montmorillonit (Veegum) as carrier have been also reported in the literature (SU and Cartensen, Jour. Pharm. Sci., 1972, 61, pp. 420–424 and Monkhouse et al., Jour. Pharm. Sci., 1972, 61, pg. 1430–1435).

The problem to be solved by the present invention is to provide an orally administrable pharmaceutical composition including a hydrophobic drug and a carrier in which the drug is quickly dissolved and adsorbed.

SUMMARY OF THE INVENTION

The problem is solved by providing a dry powder pharmaceutical composition containing a hydrophobic, poorly soluble drug that is adsorbed on to a pharmaceutical carrier preferably an organic pharmaceutical carrier such as starch or cellulose and is characterised in that the drug is present in particulate form and that the drug particles have a mean particle size of less than 10 microns and a particle size distribution such that at least 95% of particles are smaller than 15 microns.

In another aspect there is provided a process of preparing a composition, just described, which comprises the steps of mixing and drying as follows: mixing (1) a solution comprising said hydrophobic drug in a solvent for said drug (2) a suspension comprising said carrier suspended in said solvent for the drug and (3) a non-solvent for the said drug which is miscible with the said solvent for the drug said mixing being effected under suitable conditions such as for example by rapid agitation causing the precipitation of said drug having the particle-size characteristics set out above and finally (4) drying the resulting drug-carrier mixture to a dry powder form.

DETAILED DESCRIPTION OF THE INVENTION

Figure 3:

The particular hydrophobic drug used in the present invention is not critical. Any hydrophobic poorly soluble drug which is capable of existing in solid form and which can be precipitated is useful. Such drugs are described in the various pharmacopeas such as U.S.P. and other medical works. Such useful drugs also include the benzodiazepines described more fully below as the list of drugs cited from the U.S.P. XXI set out hereinabove.

According to preferred embodiments, the hydrophobic poorly soluble drug is a benzodiazepine. The term "benzodiazepine" is meant to include not only the 1,4-benzodiazepines, but also (1) the 1,4-benzodiazepine-2-ones and the 4-oxides thereof; (2) the 1,5-benzodiazepines; (3) the 2,4-benzodiazepines; (4) the triazole-1,4-benzodiazepines; (5) the heterodiazepines and (6) the pharmaceutically acceptable salts of these compounds. Illustrative benzodiazepines are listed in col. 1 of U.S. Pat. No. 4,316,897. Reference is also made to Sternbach, Progress in Drug Research, Vol. 22, Birkhauser Verlag, Basel (1978), pp. 229-266.

Benzodiazepines which may be used in this invention include alprazolam, bromazepam, camazepam, clobazepam, clonazepam, clotiazepam, chlordiazepoxid, clorazepat, diazepam, estazolam, fluorazepam, flunitrazepam, fluortemazepam, ketazolam, lorazepam, loprazolam, lormetazepam, medazepam, midazolam, nitrazepam, nimetazepam, oxazepam, oxazolam, prazepam, quazepam, triazolam and temazepam.

Particularly preferred benzodiazepines are those whose use depends on their rapid dissolution, such as oxazepam and temazepam and lormetazepam when used as hypnotics.

The pharmaceutical carrier is preferably an organic material. The pharmaceutical carrier (also sometimes referred to herein as excipient) may be one having an appropriate external surface area on which the hydrophobic drug can be precipitated from solution in fine particle form, such as starch or a microcrystalline cellulose. However, other pharmaceutical carriers may also be used such as calcium diphosphate, montmorillonite and silicates such as aerosil. The two materials of choice from the points of view of availability and price are starch and microcrystalline celluloses. Starches which may be used include finely milled starches from maize, rice and corn and other cereals as well as potato starch and cassava starch. Starch is the preferred carrier since the dissolution rate of starch containing compositions of the invention is unexpectedly higher than compositions containing other carriers.

The preferred compositions of the present invention including oxazepam are primarily suited to the treatment of sleep disorders since the release pattern of oxazepam is ideally suited to this indication. However, should the medical picture so dictate, this composition may also be used for other indications calling for oxazepam therapy, including treatment of tension, agitation and anxiety and associated autonomic disorders, i.e. use as a general tranquilizer.

In the pharmaceutical composition of the invention the carrier preferably has a particle size of less than 40 microns, more preferably less than 20 microns. The particle size will usually lie in the range of from 10 to 40 microns for the carrier. The particle size of the carrier is, however, not critical.

In accordance with the present invention the drug is "adsorbed" on to the carrier. By adsorbed, it is meant that the drug particles are closely associated with the carrier in clusters but not all of the drug particles may actually be touching the carrier particle. The hereto appended enclosed photographs 1 and 2, illustrate the typical case of oxazepam particles adsorbed, on the carrier particle of starch. This is to be distinguished from simple mixtures, where the drug particles and the carrier particles often lie independently in a non-homogeneous manner as is illustrated in the enclosed photograph 3.

The fine particle size of the absorbed hydrophobic drug is critical to the present invention. The methods of the prior art are not capable of producing the small particle size of the drug on the carrier that is produced by the method of the present invention. According to the present invention, the particle size of the adsorbed hydrophobic drug is such that the mean particle size is less than 10 microns and the distribution of particles sizes is such that at least 95% of the particles are less than 9 microns.

The size of individual particles is measured in terms of their "projected area diameter" using known methods. In one method, a composition to be tested is examined using a Scanning Electron Microscope. About 200 particles are measured in this manner and the mean and distribution of particle size are determined. Automated techniques such as those known in the art can be used. Reference is made to the "Image Analysing Systems" such as Zeiss Micro-Videomat-3 made by Carl Zeiss and the Systems Leitz A.S.B.A. and T.A.S. Plus made by Ernst Leitz Co. of Wetzlar in W. Germany.

The hydrophobic drug and the carrier may be present in the composition in any desired ratio, e.g. 1:1 or 1:2 or more. Larger or smaller ratios may of course be used, e.g. up to 1:10 but this will simply increase the bulk and expense of the composition. Ratios down to 1:0,5 can also be used.

The present invention also provides a process for the preparation of the pharmaceutical composition of the instant invention. The process according to the invention comprises mixing a solution of the hydrophobic, poorly soluble drug in a solvent for the drug as also a suspension of the carrier made also in a solvent for the drug and adding them to a non-solvent for that drug. At least one of the drug solution or the carrier suspension preferably also contains a surfactant or a wetting agent. The solvent for the drug and the non-solvent are mutually miscible under the conditions of mixing so as to precipitate the hydrophobic drug in fine particle form on the substrate.

In preferred embodiments, the solution of the drug and the suspension of the carrier are the same. In other words, the carrier is suspended in the drug solution. The two can be separated, however, and in such a case, the carrier can be suspended in a different solvent than is used for the drug solution. If the solution and suspension are separated, they can be added simultaneously or separately. If added separately, it is preferred to first add the solution of the drug and then the suspension of the carrier.

Any suitable solvent which is capable of dissolving the hydrophobic poorly water soluble drug is useful. It is, however, preferred to use ethanol or acetone as the drug solvent wherever that is possible. Where the non-solvent is water, the solvent is a water miscible solvent. Useful water miscible solvents include water miscible alcohols, ketones and amides, tetrahydrofuran, N-methyl-2-pyrolidone, dimethylsulfoxide and mixtures thereof. Particular examples of these solvents include acetone, ethyl alcohol, isopropyl alcohol, dimethylformamide, methyl ethyl ketone and similar solvents.

The non-solvent most conveniently employed for many reasons is water although other convenient non-solvents may of course be used if desirable.

Mixing takes place under conditions which cause the drug to be precipitated in very fine particle form on the carrier. Several conditions can promote the formation of fine particles. For example the drug solution and the carrier suspension should be mixed with a large volume of the non-solvent in such a manner that the concentration of the drug and the carrier is rapidly reduced at the point of introduction. This can be accomplished by slowly running the solution-suspension into a rapidly agitated volume of the non-solvent in a fine stream. By large volume of non-solvent is meant that the drug solution-carrier suspension is mixed with such a volume of the non-solvent so that it is rapidly diluted. Typically, the amount of non-solvent is between 1 and 10 times the total volume of the solution-suspension.

Another factor which can contribute to the formation of fine particles is the concentration of the drug in the solution that is mixed with the non-solvent. If the solution is high in drug concentration, preferably saturated, finer particles will result. Similarly, if the drug is forced into solution such as by heating and then is mixed with a cold non-solvent, fine particles will result. Typically, the drug solution is at a temperature of 60° C. or higher (up to the boiling point of the solvent) and the non-solvent is at a temperature of 10° to 15° C. or lower.

The drug solution and the carrier suspension can be added to the precipitation vessel through surface or subsurface delivery tubes by gravity feed or by delivery apparatus. In order to obtain rapid distribution in the precipitating vessel, specially constructed mixing devices can be used, as illustrated by U.S. Pat. Nos. 2,996,297; 3,342,605; and 3,785,777.

The surfactant or wetting agent which can be used may be any such agent which is convenient. One example of such an agent is Tween 80 (polyethyleneglycol-sorbitan-monooleate) obtainable from Atlas Chem. Division of I.C.I. America Inc. Other surfactants which can be used include polyethyleneglycol-sorbitan-monostearate as well as polyhydroxyethylene-stearate.

After the precipitation of the hydrophobic drug onto the carrier to form the adsorbate, the adsorbate can be recovered in dry form by conventional drying methods. In one convenient method, the adsorbate is simply spray dried. The drug solvent can be removed separately or at the same time as the non-solvent. Alternately, the adsorbate can be recovered by filtration, freeze drying or other suitable methods.

The normal procedure is to first prepare the pharmaceutical composition of the invention and then to add other conventional pharmaceutical carriers and excipients thereto. However, the other conventional pharmaceutical carriers and excipients can also already be present during the actual precipitation step.

The dosage unit forms of the invention for the treatment of sleep disorders contain preferably from 25 to 35 mg of oxazepam. The dosage unit forms for use as a tranquiliser may vary widely, e.g. from 5 mg to 50 mg oxazepam.

The dosage unit forms for other hydrophobic water insoluble drugs are those dosages that are conventional for those drugs. However, in some instances, similar desired effects can be achieved with lower dosages of these drugs since the compositions are rapidly dissolved.

The formulations may conveniently be presented in unit dosage and may be prepared by any of the methods well known in the pharmaceutical field.

Formulations of the present invention suitable for oral administration may be presented as discrete units such as capsules, cachets, tablets, or lozenges, each containing a predetermined amount of the pharmaceutical composition of the invention; or a suspension in an aqueous liquid or non-aqueous liquid such as syrup, an elixir, an emulsion or a draught. The pharmaceutical composition may also be presented as a bolus, electuary or paste.

A tablet may be made by compression or moulding, optionally with one or more accessory ingredients. Compressed tablets may be made by compressing in a suitable machine, the drug adsorbate mixed with other excipients such as fillers, inert diluents, lubricants and dispersing agents. These mixtures may, however, be also filled into hard gelatine capsules of suitable size.

A syrup may be made by adding the active compound to a concentrated, aqueous solution of a sugar, for example, sucrose, to which may also be added suitable accessory ingredient. Such accessory ingredient(s) may include flavorings, an agent to retard crystallization of the sugar or an agent to increase the solubility of any other ingredient, such as polyhydric alcohol, for example, glycerol or sorbitol.

Formulations for rectal administration may be presented as a suppository with a conventional carrier such as cocoa butter.

In addition to the aforementioned ingredients, the formulations of this invention may further include one or more accessory ingredient(s) selected fron diluents, buffers, flavoring agents, binders, surface active agents, lubricants, preservatives (including antioxidants) and the like. The useful amounts of such ingredients can be readily determined by those skilled in the art.

The invention will now be illustrated in more detail with particular reference to the appended photographs 1 and 2 (Photograph 3 appertaining to the Prior Art) and the following examples.

DESCRIPTION OF PHOTOGRAPHS

In the appended photographs there is shown
in Photograph 1
an electron microscope photograph of the product prepared according to example 1 given below, where 40 mm length in the photograph represents 10 microns, which shows several oxazepam particles of about 2 microns size adsorbed on a single starch particle of about 15 microns diameter
in Photograph 2,
which is also of a product prepared according to example 1 1 below, wherein 10 mm of length in the photograph represent 10 microns of length and the photograph shows an agglomerate of several starch particles on whose surface oxazepam particles of size 2–3 microns are adsorbed
in Photograph 3,
wherein a length of 4 mm in the photograph represents 1 micron and the photograph shows a physical admixture prepared according to prior art techniques by mixing starch particles with oxazepam particles in which the oxazepam particles are clearly seen quite separate and the starch particles show an exposed surface on which there is no adsorption of oxazepam particles visible.

In certain of the examples, a dissolution-test is used to illustrate the improved dissolution characteristics of the compositions of the present invention. These dissolution studies were conducted with the U.S.P. XX1 apparatus 2 employing a paddle rotating at 50 rpm and using a beaker containing one liter of 0.1N HCl at 37° C. Samples were taken periodically and their oxazepam content was determined spectrophotometrically by measuring at wavelength of 283 nm. The specific extinction value is the extinction of a 1% solution in a path length of 1 cm and for oxazepam has a value of 397 and for temazepam 350.

EXAMPLE 1

100 gm of oxazepam was suspended in 5 liters of ethanol (ca. 96%) with stirring and warming to 65° C. 10 gm of polyethyleneglycol-sorbitan-monooleate were then added with continuous stirring until a clear solution was obtained. To this solution was added 200 gm corn starch having a particle-size range from 20 to 40 microns with stirring until a uniform suspension was obtained. The suspension was then decanted in a thin slow stream at a rate of ca. 50 ml/min. into 20 liters of water with continuous rapid stirring by using a Ultra Turex stirrer having an agitation speed of 5,000 rpm. Stirring was continued further until a milky white suspension was formed. The ethanol was removed from the suspension by distillation on a rotary evaporator and the aquous suspension was then passed through a spray drier to give a fine free flowing white powder which contained 33% by weight of oxazepam adsorbed on starch particles as carrier. Size analysis made using photomicrographs of the product revealed that the mean particle size of the adsorbed oxazepam particles was 4 microns and that 95% of the particles were less than 5 microns and 100% of the particles were smaller than 8 microns.

EXAMPLE 2

The procedure of example 1 was repeated with the sole difference that acetone was used as the solvent in place of ethanol. A similar particle-size distribution was observed.

EXAMPLE 3

The procedure of example 1 was followed with the sole difference that microcrystalline cellulose or montmorillonite was used in place of starch.

EXAMPLE 4

In this example a pharmaceutical tablet formulation is given:

The fine powder material obtained in example 1 was used to prepare a tablet containing 33 mg oxazepam using the following "direct compression" formula:

| | |
|---|---|
| Oxazepam-starch adsorbate (33%) | 100.00 mg |
| Microcrystalline cellulose (Avicle 102) | 60.00 mg |
| Colloid sillica (Aerosil) | 1.00 mg |
| Lactose direct compressible | 87.00 mg |
| Magnesium stearate | 2.00 mg |
| Total weight | 250.00 mg |

The above ingredients were mixed together, passed through a sieve and directly compressed on a tablet machine into tablets of 10 mm containing 33 mg oxazepam.

A dissolution test was done on these tablets so prepared and the following results were obtained:

| Time (minutes) | 2.5 | 5.0 | 10.0 | 15.0 |
|---|---|---|---|---|
| % Oxazepam dissolved | 50.4% | 69.0% | 85.0% | 90.6% |

EXAMPLE 5

This example includes comparative data for the dissolution rate of capsules made using the composition of the present invention in comparison to commercially available Serax capsules 30 mg.

| | |
|---|---|
| Oxazepam-starch adsorbate (33%) | 90.00 mg |
| Colloidal silica (AEROSIL) | 1.00 mg |
| Lactose | 157.00 mg |
| Magnesium stearate | 2.00 mg |
| Total fill weight | 250.00 mg |

The above mixture was filled into hard gelatine capsules in which each capsule contained 30 mg oxazepam.

A dissolution test was made on the capsules so prepared with the following results:

| Time (mins.) | 5.00 | 10.00 | 15.00 | 30.00 | 60.0 |
|---|---|---|---|---|---|
| % oxazepam dissolved % Inv. | 48.00 | 65.00 | 82.00 | 95.00 | 100.00 |
| % Serax capsules | 0 | 0 | 3.00 | 12.00 | 17.00 |

"% Inv" is the % oxazepam dissolved from the preparation of the invention, whereas % Serax is the % oxazepam dissolved from the 30 mg Serax capsules.

EXAMPLE 6

A comparative in-vivo study was made in 12 healthy human volunteers using a commercially available oxazepam tablet (Seresta Fort) containing 50 mg oxazepam (tablet A) and an experimental tablet containing 25 mg oxazepam made according to example 4 (tablet B). The in-vivo study was planned as a cross-over experimental design and blood samples were taken at various time intervals after the administration of the tablets. The blood samples were then analysed for the oxazepam content, using a gas chromatography method with an electron capture detector.

The results of this comparative study are shown in the following tables I–V.

Table I shows the time course of average blood concentration of oxazepam for the 12 volunteers, using the two types of tablets for a total period of 48 hours.

Table II shows a comparison of $t_{max}$ values (the time to reach the maximum blood concentration) in the volunteers individually. It was found that, whereas the commercial tablet A took an average period of about five hours (range 1–9 hours) the experimental tablet B reached peak blood concentration within 1½ hours (range ¾–3 hours).

Tablet III shows a comparison of $C_{max}$ values (the maximum blood concentration) for the two types of oxazepam tablets. It was rather surprising to observe that almost identical peak blood concentrations (average 516–535 ng/ml) were reached in both the cases, although tablet B contained only half the dose (=25 mg oxazepam) as that contained in commercial tablet A (=50 mg oxazepam).

Table IV shows a comparison of oxazepan blood concentrations reached 10 minutes and 20 minutes respectively after administration. It can be observed that after twenty minutes, the blood concentrations of oxazepam reached with tablet B were almost four times higher than those achieved with the commercial tablet A. Evidently it is desirable for the induction of sleep and onset of hypnotic activity that a certain minimum level of drug concentration in the blood is achieved rapidly, which is possible with the tablet B, but not with commercial tablet A.

Table V shows the comparative oxazepam blood concentrations present after 9 hours and 24 hours respectively. In the case of tablet B, the drug concentration level after 9 hours fell back to a very low level, comparable to those reached with tablet A after 24 hours only. This can have an important influence for causing the side effects observed with commercial tablet A.

This pharmacokinetic study shows that an optimally formulated product containing half the dose (such as experimental tablet B) was able to show a desirable hypnotic activity with reasonably rapid onset of activity and minimal side-effects, whereas a typical sample of commercial tablet A containing twice the dose (=50 mg) of oxazepam, but in a slow-absorption formulation was unsuitable as a hypnotic agent. This series of pharmacodynamic and clinical studies made on healthy volunteers thus showed the rapid onset of sleep achieved using the pharmaceutical composition of the invention (e.g. well inside 2 hours) and that no daytime sedation or hampering of daytime activity was observed.

EXAMPLE 7

One gram of temazepam was dissolved in 30 ml of ethanol by heating to 35° C. while stirring with a magnetic stirrer. To the clear solution was added two grams of corn starch and after the addition was complete, stirring was continued for another five minutes until a uniform dispersion was formed. This warm dispersion was then poured slowly as a thin stream into 100 ml of cold demineralised water. During the addition, the water was stirred rapidly with a magnet stirrer. After the addition was complete, stirring was continued for another ten minutes. The final suspension was then passed through a spray drier to obtain a free flowing powder containing about 33% temazepam. The powder was examined under a microscope and the mean particle size of temazepam was found to be 3 microns and 95% of the particles were less than 5 microns.

The resulting powder was then formulated in a manner similar to example 5 and containing 10 mg temazepam filled into hard-gelatine capsules and compared for dissolution-rate with the commercially available Normison (Wyeth) soft-gelatine capsules containing 10 mg temazepam and Restoril (Sandoz AG) hard gelatine capsules containing 15 mg temazepan.

The dissolution rate test was done by using U.S.P. XXI apparatus No. 1 (basket) rotating at 100 rpm and using a beaker containing 900 ml of 0.1N HCl at 37° C. Samples were measured spectrophotometrically at a wavelength of 280 nm; E 1%=350.

The results of this dissolution study were as following:

| Time (mins.) | 2.5 | 5.0 | 10.0 | 15.0 |
|---|---|---|---|---|
| % Temazepam dissolved | | | | |
| (1) Exper. Hard capsule 10 mg | 64.0% | 89.2% | 99.0% | |
| (2) Normison soft capsule 10 mg | 1.0 | 51.0% | 95.0 | |
| (3) Restorit hard capsule 15 mg | 4.1 | 6.0% | 16.7% | 63.8% |

TABLE I

| | Average blood concentration of oxazepam (ng/ml) | | | |
|---|---|---|---|---|
| | Commercial Tablet A 50 mg oxazepam | | Experimental Tablet B 25 mg oxazepam | |
| Time | Average | Range | Average | Range |
| 10.0 min. | 4.7 | (ND-5.0) | 26.25 | (ND-99) |
| 20.0 min. | 40.5 | (ND-214) | 159.5 | (ND-329) |
| 30.0 min. | 83.3 | (ND-280) | 290.1 | (9-534) |
| 45.0 min. | 197.0 | (11-399) | 370.0 | (21-655) |
| 1.0 hrs. | 261.3 | (26-480) | 438.1 | (69-742) |
| 1½ hrs. | 328.0 | (89-840) | 438.3 | (105-673) |
| 2.0 hrs. | 376.6 | (202-914) | 400.0 | (211-601) |
| 3.0 hrs. | 453.4 | (235-916) | 409.5 | (202-798) |
| 4.0 hrs. | 467.8 | (242-722) | 342.5 | (142-705) |
| 6.0 hrs. | 421.2 | (244-728) | 246.5 | (95-514) |
| 9.0 hrs. | 373.3 | (174-685) | 156.7 | (45-376) |
| 12.0 hrs. | 301.5 | (113-576) | 106.7 | (30-270) |
| 24.0 hrs. | 157.5 | (69-382) | 34.6 | (ND-115) |
| 34.0 hrs. | 73.1 | (4-216) | 15.0 | (ND-59) |
| 48.0 hrs. | 28.5 | (ND-91) | 16.6 | (ND-25) |

ND = not detectable (≦2 ug/ml)

Comparison of the time to reach maximum blood concentration ($T_{max}$) of oxazepam in 12 human volunteers:

TABLE II

| Subject | Commercial Tablet A 50 mg oxazepam | Experimental Tablet B 25 mg oxazepam |
|---|---|---|
| 1 | 6.0 hours | 1.5 hours |
| 2 | 1.0 hours | 0.75 hours |
| 3 | 4.0 hours | 1.5 hours |
| 4 | 4.0 hours | 3.0 hours |
| 5 | 3.0 hours | 3.0 hours |
| 6 | 9.0 hours | 1.0 hours |
| 7 | 4.0 hours | 1.5 hours |
| 8 | 9.0 hours | 1.0 hours |
| 9 | 2.0 hours | 1.0 hours |
| 10 | 6.0 hours | 1.5 hours |
| 11 | 9.0 hours | 2.0 hours |
| 12 | 4.0 hours | 1.0 hours |
| Average | 5.0 hours | 1.55 hours |
| Range | (1.9-9.0) | (0.75-3.0) |

Comparison of the maximum blood concentration ($C_{max}$) of oxazepam (ng/ml) in 12 human volunteers:

TABLE III

| Subject | Commercial Tablet A 50 mg oxazepam | Experimental Tablet B 25 mg oxazepam |
|---|---|---|
| 1 | 664.0 ng/ml | 410.0 ng/ml |
| 2 | 480.0 ng/ml | 459.0 ng/ml |
| 3 | 315.5 ng/ml | 431.0 ng/ml |
| 4 | 834.5 ng/ml | 798.0 ng/ml |
| 5 | 915.0 ng/ml | 406.0 ng/ml |
| 6 | 329.9 ng/ml | 552.0 ng/ml |
| 7 | 583.0 ng/ml | 536.0 ng/ml |
| 8 | 435.0 ng/ml | 623.0 ng/ml |
| 9 | 572.0 ng/ml | 533.0 ng/ml |
| 10 | 244.0 ng/ml | 294.0 ng/ml |
| 11 | 335.0 ng/ml | 416.0 ng/ml |
| 12 | 722.0 ng/ml | 742.0 ng/ml |
| Average | 535 ng/ml | ng/ml |
| Range | (244-915) | (294-798) |

Comparison of blood concentration of oxazepam (ng/ml) reached after 10 minutes and 20 minutes in 12 human volunteers:

TABLE IV

| | $C_{10\text{ minutes}}$ | | $C_{20\text{ minutes}}$ | |
|---|---|---|---|---|
| Subject | Comm. Tab. A (50 mg) | Exp. Tab. B (25 mg) | Comm. Tab. A (50 mg) | Exp. Tab. B (25 mg) |
| 1 | ND (≦2) | 24 | 12 | 235 |
| 2 | ND (≦2) | 35 | 6 | 116 |
| 3 | ND (≦2) | 19 | ND (≦2) | 120 |
| 4 | 5 | 7 | 16 | 64 |
| 5 | ND (≦2) | ND (≦2) | ND (≦2) | ND (≦2) |
| 6 | 23 | 19 | 77 | 82 |
| 7 | ND (≦2) | 99 | ND (≦2) | 329 |
| 8 | ND (≦2) | ND (≦2) | ND (≦2) | 193 |
| 9 | 3.5 | 47 | 214 | 221 |
| 10 | 25 | 50 | 50 | 163 |
| 11 | ND (≦2) | ND (≦2) | 68 | 149 |
| 12 | ND (≦2) | 15 | 44 | 243 |
| Average | 4.7 | 26.25 | 40.5 | 159 |
| Range | (ND-25) | (ND-99) | (ND-214) | (ND-243) |

Comparison of blood concentration of oxazepam (ng/ml) reached after 9 hours and 24 hours in 12 human volunteers:

TABLE V

| | $C_{9\text{ hours}}$ | | $C_{24\text{ hours}}$ | |
|---|---|---|---|---|
| Subject | Comm. Tab. A (50 mg) | Exp. Tab. B (25 mg) | Comm. Tab. A (50 mg) | Exp. Tab. B (25 mg) |
| 1 | 572 | 188 | 214 | 44 |
| 2 | — | 129 | 207 | 50 |
| 3 | 174 | 66 | 74 | 8 |
| 4 | 685 | 376 | 260 | 115 |
| 5 | 277 | 118 | 158 | ND (≦2) |
| 6 | 329 | 164 | 91 | 14 |
| 7 | 340 | 95 | 145 | 56 |
| 8 | 435 | 363 | 382 | 91 |
| 9 | 176 | 73 | 100 | 15 |
| 10 | 194 | 45 | 80 | 16 |
| 11 | 335 | 135 | 69 | 7.5 |
| 12 | 590 | 129 | 110 | ND (≦2) |
| Average | 373 | 156 | 157 | 34 |
| Range | (685-174) | (376-45) | (382-69) | (115-2) |

What is claimed is:

1. A pharmaceutical composition for oral administration comprising a hydrophobic practically water-insoluble benzodiazepene drug adsorbed onto a pharmaceutical carrier having an average particle size of less than 40 microns wherein the drug is present in particulate form and the particles of the drug have a mean particle size of less than 10 microns and a particle size distribution such that at least 95% of the particles are less than 15 microns.

2. The pharmaceutical composition as claimed in claim 1, wherein the hydrophobic practically water insoluble drug is a benzodiazepine.

3. A pharmaceutical composition as claimed in claim 1, wherein said carrier has an average particle size of less than 20 microns.

4. A pharmaceutical composition as claimed in claim 3, wherein the carrier is an organic material.

5. A pharmazeutical composition as claimed in claim 1, wherein the hydrophobic drug is alprazolam, bromazepam, camazepam, clobazepam, clonazepam, clotiazepam, chlordiazepoxid, clorazepat, diazepam, estazolam, flurazepam, flunitrazepam, fluortemazepam, ketazolam, lorazepam, loprazolam, lormetazepam, medazepam, midazolam, nitrazepam, nimetazepam, oxazepam, oxazolam, prazepam, quazepam, triazolam and temazepam.

6. A pharmaceutical composition as claimed in claim 1, wherein the pharmaceutical carrier is starch.

7. A pharmaceutical composition as claimed in claim 1, wherein the pharmaceutical carrier is microcrystalline cellose.

8. A pharmaceutical composition as claimed in claim 1, wherein said hydrophobic practically insoluble drug is 7-chloro-1,3-dihydro-3-hydroxy-5-phenyl-2H-1,4-benzodiazepine-2-one.

9. A pharmaceutical composition as claimed in claim 1, wherein said hydrophobic practically insoluble drug is 7-chloro-1,3-dihydro-3-hydroxy-1-methyl-5-phenyl-2H-1,4-benzo diazepine-2-one.

10. A pharmaceutical composition as claimed in claim 1, wherein the ratio of hydrophobic drug to pharmaceutical carrier is 1:1 to 1:10.

11. A pharmaceutical composition as claimed in claim 10, wherein the ratio is from 1:1 to 1:2.

12. A process of preparing a composition comprising a hydrophobic practically water insoluble drug adsorbed onto a carrier having an average particle size of less than 40 microns, wherein the drug is present in particulate form and the particles of the drug have a mean particle size less than 10 microns and a distribution of particle sizes such that at least 95% of the particles are less than 15 microns, which process comprises the step of mixing (1) a solution comprising said hydrophobic drug in a solvent for said drug, (2) a suspension comprising said carrier suspended in said solvent and (3) a non-solvent for said drug which is miscible with said solvent for the drug and said mixing being under conditions which cause the precipitation of said drug having the said particle size characteristics, and (4) recovering the drug-carrier adsorbate by drying.

13. A process according to claim 12, wherein said solution and said suspension in steps (1) and (2) form a single solution-suspension.

14. A process according to claim 13, wherein the solution or the suspension also contains a surfactant.

15. A process according to claim 13, wherein the surfactant is polyethyleneglycol sorbitan monooleate.

16. A process according to claim 12, wherein the nonsolvent is water.

17. A process according to claim 12, wherein said drug solution and said carrier suspension are added to a large volume of said non-solvent in the form of a fine stream under conditions of rapid stirring.

18. A process according to claim 12, wherein said drug solution is at a higher temperature than said non-solvent.

19. A process according to claim 12, wherein said drug solution is saturated with said hydrophobic drug.

20. A process according to claim 11, wherein said drug solvent is selected from the group consisting of acetone, ethanol and methanol.

21. A process according to claim 11, wherein said drug-carrier adsorbate is recovered by spray drying.

22. A process according to claim 11, wherein said drug-carrier adsorbate is recovered by filtration and drying.

23. A process according to claim 11, wherein said solution of drug is added to said non-solvent separately from said suspension of said carrier.

24. A process according to claim 11, wherein said solution is added first and said suspension is added second.

25. A method of treating mammals for sleep disorders or tranquillizing which comprises orally administering to said mammal, in dosage unit medicament form, a dosage unit containing a hydrophobic practically water insoluble benzodiazepine drug adsorbed onto a pharmaceutical carrier, characterised in that the drug is present in particulate form and the particles of the drug have a mean particle size less than 10 microns and a distrbution of particle sizes such that at least 95% of the particles are less than 15 microns, and the carrier has an average particle size distribution of less than 40 microns.

26. A method of treating sleep disorders which comprises orally administering to a subject, in dosage unit medicament form, a dosage unit containing 7-chloro-1,3-dihydro-3-hydroxy-5-phenyl-2H-1,4-benzodiazepine-2-one adsorbed onto a pharmaceutical carrier, characterised in that the drug is present in particulate form and the particles of the drug have a mean particle size less than 10 microns and a distribution of particle sizes such that at least 95% of the particles are less than 15 microns, and the carrier has an average particle size of less than 40 microns.

27. A method as claimed in claim 26, wherein the dosage unit medicament form contains 25–40 mg of oxazepam.

28. A method according to any of claims 25, 26 or 27, wherein said carrier is starch and/or microcrystalline cellulose.

* * * * *